United States Patent
Hsu et al.

(10) Patent No.: US 8,979,738 B2
(45) Date of Patent: Mar. 17, 2015

(54) DEVICES AND METHODS FOR REMOVAL OF DEBRIS FROM THE OBJECTIVE LENS OF AN ENDOSCOPE

(75) Inventors: Thomas Hsu, Foster City, CA (US); Senzan Hsu, Foster City, CA (US)

(73) Assignee: Medeon Biosurgical, Inc., Los Altos, CA (US)

( * ) Notice: Subject to any disclaimer, the term of this patent is extended or adjusted under 35 U.S.C. 154(b) by 648 days.

(21) Appl. No.: 12/663,573

(22) PCT Filed: May 31, 2008

(86) PCT No.: PCT/US2008/006923
§ 371 (c)(1),
(2), (4) Date: Dec. 8, 2009

(87) PCT Pub. No.: WO2008/153841
PCT Pub. Date: Dec. 18, 2008

(65) Prior Publication Data
US 2010/0174144 A1    Jul. 8, 2010

Related U.S. Application Data

(60) Provisional application No. 60/933,693, filed on Jun. 8, 2007.

(51) Int. Cl.
*A61B 1/00*      (2006.01)
*A61B 1/012*    (2006.01)
(Continued)

(52) U.S. Cl.
CPC .............. *A61B 1/012* (2013.01); *A61B 1/00087* (2013.01); *A61B 1/00135* (2013.01); *A61B 1/126* (2013.01); *A61B 1/3132* (2013.01); *A61B 1/00142* (2013.01)

USPC ........... 600/122; 600/121; 600/133; 600/157; 600/169; 600/176

(58) Field of Classification Search
USPC .......... 600/121–125, 133, 157, 169, 175–176
See application file for complete search history.

(56) References Cited

U.S. PATENT DOCUMENTS 3,145,249 A * 8/1964 Meltzer ........................ 359/508
4,524,920 A     6/1985 Kidawara et al.
(Continued)

FOREIGN PATENT DOCUMENTS

EP    0648044 A1   10/1997
EP    1153567 A1   11/2001
(Continued)

OTHER PUBLICATIONS

Supplementary European Search Report dated Feb. 6, 2013 in corresponding European Patent Application No. EP08768019.

*Primary Examiner* — Matthew J Kasztejna
(74) *Attorney, Agent, or Firm* — Dergosits & Noah LLP; Todd A. Noah

(57) ABSTRACT

The invention encompasses devices and methods used to keep the objective lens of a viewing or illuminating device, specifically an endoscope, free from obstructive fluid and dirt; specifically a device having a hollow body designed to fit over an endoscope, and a transparent lens cover film that is retained within the device and that is threaded in front of the objective lens of an endoscope, thereby maintaining a clear and unobstructed transparent window in front of the endoscope lens.

9 Claims, 2 Drawing Sheets

(51) Int. Cl.
*A61B 1/12* (2006.01)
*A61B 1/313* (2006.01)

(56) References Cited

U.S. PATENT DOCUMENTS

| | | | |
|---|---|---|---|
| 5,167,220 A | 12/1992 | Brown | |
| 5,207,213 A | 5/1993 | Auhll et al. | |
| 5,225,001 A | 7/1993 | Manni et al. | |
| 5,339,800 A * | 8/1994 | Wiita et al. | 600/109 |
| 5,363,843 A * | 11/1994 | Daneshvar | 128/897 |
| 5,392,766 A * | 2/1995 | Masterson et al. | 600/157 |
| 5,400,767 A | 3/1995 | Murdoch | |
| 5,464,008 A | 11/1995 | Kim | |
| 5,469,841 A | 11/1995 | Kobayashi et al. | |
| 5,514,084 A | 5/1996 | Fisher | |
| 5,549,543 A | 8/1996 | Kim | |
| 5,575,756 A | 11/1996 | Karasawa et al. | |
| 5,830,127 A | 11/1998 | DeCastro | |
| 6,017,333 A | 1/2000 | Bailey | |
| 6,258,025 B1 * | 7/2001 | Swallert | 600/157 |
| 6,354,992 B1 | 3/2002 | Kato | |
| 6,447,444 B1 * | 9/2002 | Avni et al. | 600/121 |
| 6,447,446 B1 | 9/2002 | Smith et al. | |
| 6,712,479 B1 | 3/2004 | Seitzinger et al. | |
| 6,755,782 B2 * | 6/2004 | Ogawa | 600/127 |
| 6,923,759 B2 * | 8/2005 | Kasahara et al. | 600/157 |
| 8,088,065 B2 * | 1/2012 | Karasawa et al. | 600/157 |
| 2003/0109837 A1 | 6/2003 | McBride-Sakal | |
| 2006/0020165 A1 * | 1/2006 | Adams | 600/121 |
| 2007/0049794 A1 | 3/2007 | Glassenberg et al. | |
| 2008/0081948 A1 * | 4/2008 | Weisenburgh et al. | 600/121 |

FOREIGN PATENT DOCUMENTS

| | | |
|---|---|---|
| GB | 2188746 A | 10/1987 |
| JP | 61069019 | 4/1986 |
| JP | 2005052229 | 3/2005 |
| JP | 2007105314 A | 4/2007 |
| WO | 9220274 A1 | 11/1992 |
| WO | 9532012 A1 | 11/1995 |
| WO | 2008153841 A2 | 12/2008 |

* cited by examiner

DEVICES AND METHODS FOR REMOVAL OF DEBRIS FROM THE OBJECTIVE LENS OF AN ENDOSCOPE

FIELD OF THE INVENTION

The invention relates to devices that keep the objective lens of a viewing or illuminating device, specifically an endoscope clear of debris while in use without the need for removing the endoscope from the body of the patient. In addition, a variation of the invention prevents direct contact of the endoscope surface and body tissue surface, thereby eliminating the need for sterilization of the endoscope.

BACKGROUND

Certain medical procedures require the insertion of a viewing device, an "endoscope", into a body cavity in order to view features and structures within the body cavity. Such an endoscope may be, for example, a gastroscope, pharyngoscope, laryngoscope, laparoscope, colonoscope or any other type of medical telescope. For the purpose of this disclosure, we shall use the term "endoscope" to include any viewing device that is inserted into the body of a subject and used to view internal structures. The endoscope may be rigid or flexible. Rigid endoscopes, such as standard laparoscopes, usually consist of a shaft of approximately 300-500 mm length, with an outer diameter of 5 mm to 12 mm, having an objective lens at one end and an eyepiece at the other end. In some instances, such as with fiber-optic gastroscopes, the device may be over a meter in length and may permit flexion and manipulation by the operator of the distal end. The shaft of the endoscope often contains light-transmitting fiber-optic bundles and/or lenses that transmit visual signals and light.

The endoscope also normally has a connection, adjacent to the eyepiece, for the attachment of an external light source which provides illumination, via light-transmitting fibers within the endoscope.

Prior to the introduction of a rigid endoscope, such as a laparoscope, the body cavity is generally inflated with a gas, usually carbon dioxide, using a gas insufflator.

Subsequently a plastic or metal sleeve or sheath, often referred to as a trocar, is inserted through the wall of the cavity. These sleeves contain a means of making a seal to prevent the leakage of gas from within the body cavity. The end of the endoscope containing the objective lens is inserted into the body cavity through the sleeve, the attached light-source activated and the features within the body cavity viewed through the eyepiece of the endoscope or on a video monitor receiving signals from a video camera attached to the eyepiece.

The objective lens of the endoscope often becomes soiled during operative procedure. Tissue particles, blood, mucous and other body fluids attach to the lens and obscure vision. The usual routine when such problem arises is to remove the endoscope from the patient's body and soak its distal end (the lens) in sterile water, wipe the lens with a sterile towel, and reinsert the laparoscope into the patient's body through the existing laparoscopic trocar. During some operative procedures, the endoscope may have to be removed frequently to have the lens wiped clean.

The loss of vision due to soiling of the objective lens of the endoscope can be a serious problem, especially if it occurs at a critical moment during surgery. It increases the time required for a procedure and necessitates repeated withdrawal and insertion of the endoscope which may produce trauma to the tissues. The covering of the objective lens of the endoscope by blood is often referred to as the "red video" sign. This is particularly serious if the bleeding is extensive and if time is wasted in removing, cleaning, and reinserting the lens. If clean, unobstructed lens is not available quickly enough for identification and control of the bleeding source, the procedure is more likely to be converted to an emergency "open" operative procedure requiring large surgical incisions.

A number of solutions have been developed for keeping the objective lens free of soiling. These include the use of water jets, ultrasound devices, liquid irrigation, and brushes (see U.S. Pat. Nos. 5,207,213, 5,549,543, 5,225,001, 5,167,220, 5,400,767, 5,514,084, 5,575,756, 5,830,127, 6,017,333, 6,354,992, 6,447,446, and patent publications US23109837A1, WO09220274A1, WO09532012A1) There are also several devices that solve the problem of fogging of the objective lens (see U.S. Pat. Nos. 5,549,543, 5,464,008, 6,712,479, and patent publication EP01153567A1). None of these describe or suggest the present invention.

There is clearly a Long-felt need for devices and methods that maintain a clear and unobstructed view through the objective lens of an endoscope while in use; devices that clear obstructive fluids and debris from the optical/visual path of an endoscope while in use; and devices that eliminate the need for the endoscope to be withdrawn from the patient in order that the objective lens may be cleaned. There is a need for such devices that are simple and inexpensive to manufacture, that are simple to use and robust in use, and that can be used with a variety of endoscopic devices. The present invention provides such devices and methods of using them.

GENERAL DESCRIPTION

The invention encompasses devices and methods used to keep the objective lens of an endoscope, for example a laparoscope, free from debris, fluid and dirt.

The device can work equally with any type of viewing apparatus or illuminating apparatus to maintain a clear and unobstructed optical path.

In certain embodiments, the body of the device is a hollow tube or sheath designed to receive an endoscope within its lumen. The device is designed such that, in use, the distal end of the endoscope, having the objective lens there-disposed, is positioned within the lumen of the device at or near the distal tip of the body of the device.

Certain embodiments include a lens cover film wound onto a spool. For example, a flexible lens cover film may be rolled onto a first spool and systematically unrolled such that it passes in front of the objective lens of the endoscope. The lens cover film can be unrolled as needed to provide a clean and clear lens cover in front of the objective lens. The leading end of the lens cover film may be captured and wound onto on a second spool. By winding the lens cover film onto the second spool, the lens cover film is pulled from the first spool, along a pre-set travel path, passing in front of the objective lens, and wound onto the second spool. The travel path may be defined by guides of various design sufficient to hold and guide the lens cover film along the pre-set travel path. The guide may include rails or slits through which the lens cover film passes. The guide is generally constructed as an integral part of the body of the device. The guide may be supported with additional frames, scaffolds, or other device tip designs to provide a flat surface to the portion of the film in front of the lens. The guide and body of the device are further described in the detailed description.

The device may have additional frames, scaffolds, or specific distal tip design to allow the surface of lens cover film to become parallel to the surface of the objective lens at the distal end of the endoscope.

The device of the invention may optionally be incorporated into the structure of a viewing device such as an endoscope so that the endoscope and the device function as a single integrated apparatus.

The device of the invention may cover most or all of the endoscope (including the distal end of the endoscope) to provide complete physical barrier between the endoscope and body tissues, thereby preventing the need for sterilization of the endoscope prior to the actual endoscopic procedure.

The device of the invention may have additional slits or tubular channels (other than those for the passage of the film covering the lens to achieve a clear, unobstructed view during the endoscope use) to allow passage of endoscopic instruments such as biopsy forceps or brushes, air, fluids, or debris such as mucus or other bodily materials. Air may be removed from or pumped into the body cavity via such slits or channels that travel along the body of the device. Fluids may be removed from or irrigated into the body cavity via such slits or channels that travel along the body of the device. Debris may be removed from the body cavity via such slits or channels. Such slits or channels may have openings at the distal end of the device body, thereby allowing endoscopic instrumentation and allowing suction, irrigation, and other functions related to passage of air, fluids, and debris at the distal end of the endoscope.

Certain embodiments include additional openings, valves, dials, buttons, or controls of various designs near the proximal end of the device body (surrounding the proximal end of the endoscope), in the vicinity of the spools controlling the passage of the lens film, to allow passage of endoscopic instruments and/or to control the passage of air, fluids, or debris through the additional slits or channels that travel along and are an integral part of the device body.

Certain embodiments include a rigid device body while other embodiments include a flexible device body. Flexible device body design may be more appropriately used for flexible endoscopes.

Certain embodiments include wipers that physically wipe fluid and debris from the objective lens. Such wipers move in front of the lens or lens cover to mechanically remove debris. Wipers include flexible blades and brushes. Wipers may move in any fashion that is effective to remove debris.

A specific example of the current invention is: a device for maintaining a clear optical path immediately in front of the lens of an elongated viewing apparatus, the device comprising: an elongated hollow body defining comprising a proximal end and a distal end, wherein the elongated hollow body defines a lumen, wherein the elongated hollow body is adapted to receive the elongated viewing apparatus, a guide element disposed within the elongated hollow body, and a transparent lens cover film movably (for example slidably) associated with the guide element wherein the transparent lens cover film is threaded through and guided by the guide element so as to describe a preset travel path passing immediately in front of the lens of the elongated viewing apparatus.

Note that although the type of viewing apparatus described in the examples is generally elongated, thus requiring the device of the invention to be elongated, the current invention is not limited to en elongated embodiment. Additionally, the word "elongated" is not meant to limit the device to any particular dimensions, merely to indicate that the device has a length that generally exceeds its diameter, and the device of the invention encompasses all embodiments employing a means of removing debris from in front of a viewing device or an illuminating device.

Another specific example of the current invention is: a device for maintaining a clear optical path immediately in front of the lens of an elongated viewing apparatus, the device comprising: an elongated hollow body comprising a proximal end and a distal end, wherein the elongated hollow body is adapted to receive the elongated viewing apparatus, a guide element disposed within the elongated hollow body, a transparent lens cover film movably (for example slidably) associated with the guide element wherein the transparent lens cover film is threaded through and guided by the guide element so as to describe a preset travel path passing immediately in front of the transparent distal end of the device body and the lens of the elongated viewing apparatus, and a frame/scaffold/lens cover film support means or specific distal device tip design to allow the surface of lens cover film become parallel to the surface of the lens of the elongated viewing apparatus.

Another specific example of the current invention is: a device for maintaining a clear optical path immediately in front of the lens of an elongated viewing apparatus, the device comprising: an elongated hollow body comprising a proximal end and a distal end, wherein the elongated hollow body defines a lumen, wherein the distal end is transparent and has a wall or bather separating the lumen from device exterior surface, wherein the elongated hollow body is adapted to receive the elongated viewing apparatus, a guide element disposed within the elongated hollow body, a transparent lens cover film movably (for example slidably) associated with the guide element wherein the transparent lens cover film is threaded through and guided by the guide element so as to describe a preset travel path passing immediately in front of the transparent distal end of the device body and the lens of the elongated viewing apparatus.

Another specific example of the current invention is: a device for maintaining a clear optical path immediately in front of the lens of an elongated viewing apparatus, the device comprising: an elongated hollow body comprising a proximal end and a distal end, wherein the elongated hollow body defines a lumen, wherein the distal end is transparent and has a wall or barrier separating the lumen from device exterior surface, wherein the elongated hollow body is adapted to receive the elongated viewing apparatus, a guide element disposed within the elongated hollow body, a transparent lens cover film movably (for example slidably) associated with the guide element wherein the transparent lens cover film is threaded through and guided by the guide element so as to describe a preset travel path passing immediately in front of the transparent distal end of the device body and the lens of the elongated viewing apparatus.

Another specific example of the current invention is: a device for maintaining a clear optical path immediately in front of the lens of an elongated viewing apparatus, the device comprising: an elongated hollow body comprising a proximal end and a distal end, wherein the elongated hollow body defines a lumen, wherein the distal end is transparent and has a wall or barrier separating the lumen from device exterior surface, wherein the elongated hollow body is adapted to receive the elongated viewing apparatus, a guide element disposed within the elongated hollow body, a transparent lens cover film movably (for example slidably) associated with the guide element wherein the transparent lens cover film is threaded through and guided by the guide element so as to describe a preset travel path passing immediately in front of the transparent distal end of the device body and the lens of the elongated viewing apparatus, an additional guide element or additional guide elements disposed within the elongated hollow body for passage of air, fluids, debris, or endoscopic instruments.

Another specific example of the current invention is: a device for maintaining a clear optical path immediately in front of the lens of an elongated viewing apparatus, the device comprising: an elongated hollow body comprising a proximal end and a distal end, wherein the elongated hollow body defines a lumen, wherein the elongated hollow body is adapted to receive the elongated viewing apparatus, a movable wiper operably attached to the elongated hollow body wherein the wiper moves through a path immediately in front of the lens of the elongated viewing apparatus, thereby removing obstructive debris and maintaining a clear optical path immediately in front of the lens of the elongated viewing apparatus.

The term "immediately" does not limit the distance between the lens and the lens cover film, but merely implies that the lens cover film is positioned in front of the lens. It is expressly stated that other elements, such as a lens cover, may be present between the lens and the lens cover film. However, in certain embodiments, the lens cover may be absent.

Exemplary embodiments of the invention are described in detail by the figures and by the description below.

THE FIGURES

FIG. 1 is a schematic longitudinal cross-section of the device showing the endoscope body (1), the objective lens (2), the lens cover film (3), the first spool (4) and the second spool (5).

FIG. 2A is a schematic view of one embodiment of the device showing the device body (6) wherein the device body defines internal guide channels (9) through which the lens cover film (3) is threaded. The lens cover film emerges out through a first guide slit (7), passes in front of the lens cover (22) and passes back into a second guide slit (8). In this view the endoscope body (1) and the objective lens (2) can be seen accommodated within the lumen of the device. The transparent lens cover (22) may be absent in other embodiments.

Figure 1:
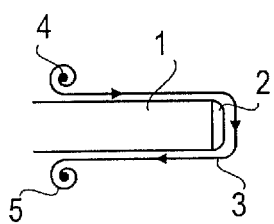
Figure 2A:
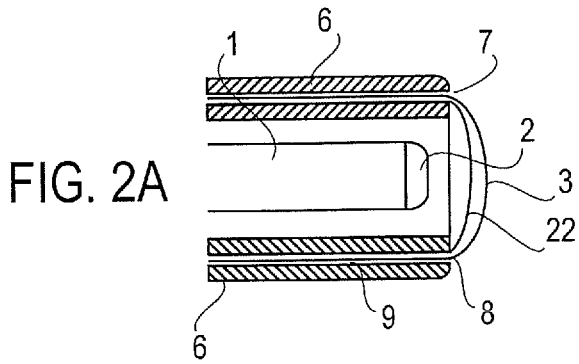
FIG. 2B is a schematic head-on view of the device showing the endoscope body (1), the objective lens (2), the lens cover film (3), device body (6), a first guide slit (7), a second guide slit (8). The lens cover (22) is not shown in this figure.
FIG. 2C is a perspective external view of the device showing the lens cover film (3) threaded out of the first guide slit (7) and back into the second guide slit (8), passing in front of the objective lens (not shown).
Figure 2B:
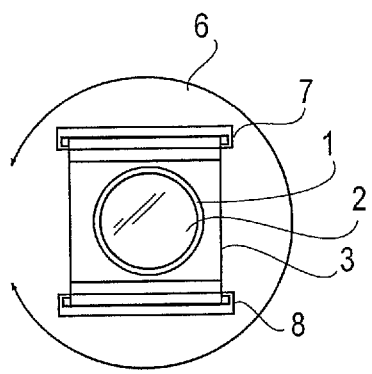
Figure 2C:
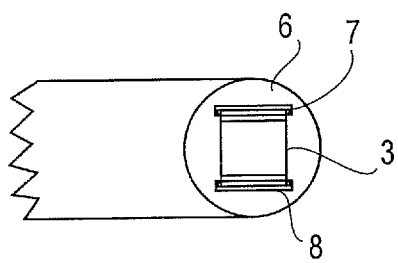
Figure 3:
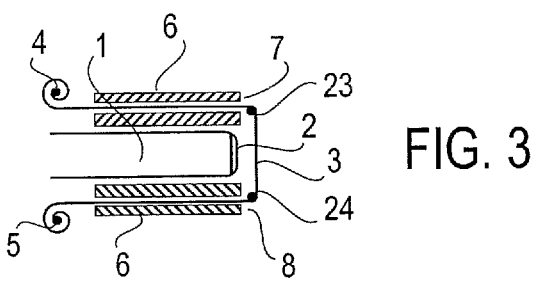

FIG. 3 is a schematic longitudinal cross-section of one embodiment of the device showing the endoscope body (1), the objective lens (2), the lens cover film (3), the first spool (4), the second spool (5), device body (6), first guide slit (7), second guide slit (8), upper frame supporting lens cover film (23), and lower frame supporting lens cover film (24). The lens cover film emerges out through a first guide slit (7), wraps around upper frame (23), passes in front of the lens (2), wraps around lower frame (24), and passes back into a second guide slit (8). In this view the endoscope body (1) and the objective lens (2) can be seen accommodated within the lumen of the device. The upper frame (23) and lower frame (24) allow the surface of the lens cover film (3) become parallel to the surface of objective lens (2). The lens cover (22) is not present in this embodiment and may be absent in other embodiments.

Figure 4A:
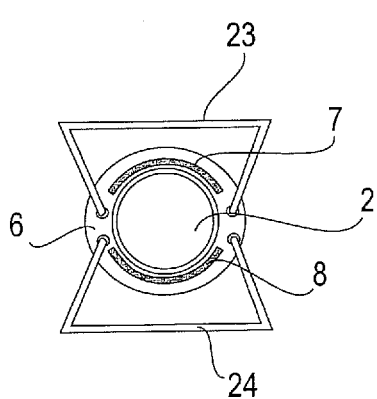

FIG. 4A is a schematic head-on view of the device showing the objective lens (2) inside the device body lumen, device body (6), a first guide slit (7), a second guide slit (8), upper frame supporting lens cover film (23), and lower frame supporting lens cover film (24). The lens cover film (3) is omitted in this figure in order to clearly demonstrate the 2 guide slits (with curvilinear or arc cross-sectional orientation in this embodiment). However, lens cover film (3) is present in and is an integral part of the present embodiment.

Figure 4B:
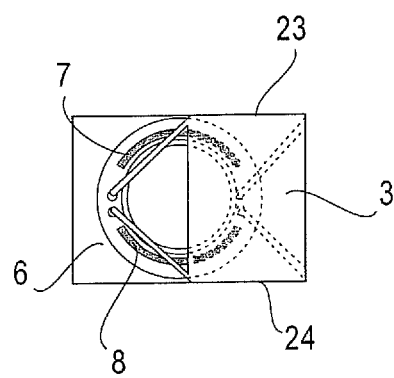

FIG. 4B is a perspective external view of the device showing the lens cover film (3) threaded out of the first guide slit (7), wraps around upper frame (23), passes in front of the objective lens (not shown), wraps around lower frame (24), and back into the second guide slit (8). The upper frame (23) and lower frame (24) are attached to device body (6) and allow the surface of the lens cover film (3) become parallel to the surface of objective lens (not shown).

Figure 5:
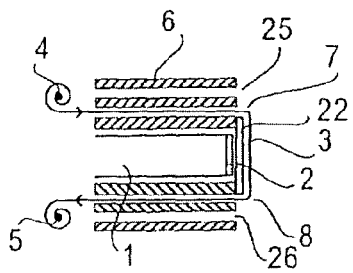

FIG. 5 is a schematic longitudinal cross-section of one embodiment of the device showing the endoscope body (1), the objective lens (2), the lens cover film (3), the first spool (4), the second spool (5), device body (6), first guide slit (7), second guide slit (8), transparent lens cover (22), first additional guide slit/channel (25), and second additional guide slit/channel (26). The 2 additional slits/channels traverse along the device body and may allow passage of air, fluids, debris, or endoscopic instruments. The lens cover film emerges out through a first guide slit (7), passes in front of the lens (2) and passes back into a second guide slit (8). In this view the endoscope body (1) and the objective lens (2) can be seen accommodated within the lumen of the device with transparent lens cover (22). The lens cover (22) may be absent in other embodiments.

Figure 6A:
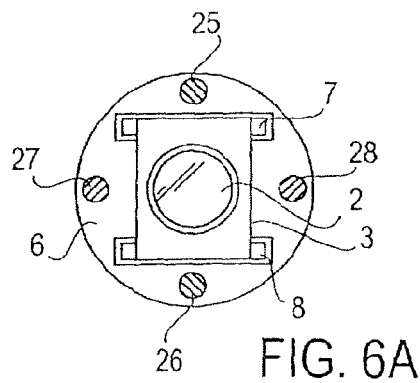

FIG. 6A is a schematic head-on view of the device showing the objective lens (2) inside the device body lumen, lens cover film (3), device body (6), a first guide slit (7), a second guide slit (8), first additional guide slit/channel (25), second additional guide slit/channel (26), third additional guide slit/channel (27), and fourth additional guide slit/channel (28). Any of the additional slits/channels may allow passage of air, fluids, debris, or endoscopic instruments. The number and location of the additional slits/channels may vary or may be absent in other embodiments. The transparent lens cover (22) is not shown but is present in certain embodiments including the present embodiment.

Figure 6B:
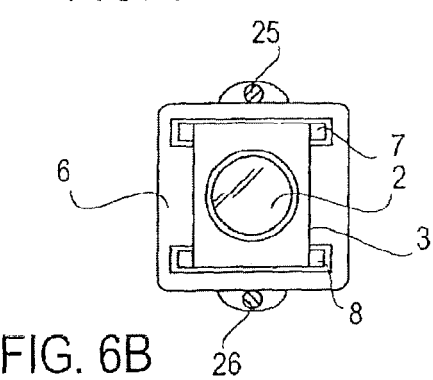

FIG. 6B is a schematic head-on view of the device showing the objective lens (2) inside the device body lumen, lens cover film (3), device body (6), a first guide slit (7), a second guide slit (8), first additional slit/channel (25), and second additional slit/channel (26). Any of the additional slits/channels may allow passage of air, fluids, debris, or endoscopic instruments. The number and location of the additional slits/channels may vary or may be absent in other embodiments. The transparent lens cover (22) is not shown but is present in certain embodiments including the present embodiment.

Figure 6C:
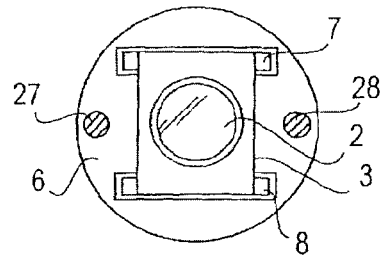

FIG. 6C is a schematic head-on view of the device showing the objective lens (2) inside the device body lumen, lens cover film (3), device body (6), a first guide slit (7), a second guide slit (8), first additional slit/channel (27), and second additional slit/channel (28). Any of the additional slits/channels may allow passage of air, fluids, debris, or endoscopic instruments. The number and location of the additional slits/channels may vary or may be absent in other embodiments. The transparent lens cover (22) is not shown but is present in certain embodiments including the present embodiment.

Figure 7:
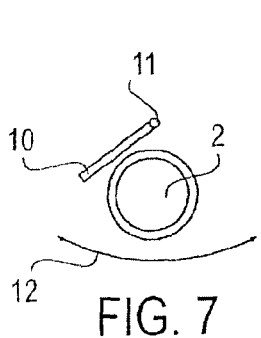

FIG. 7 is a schematic head-on view of the device showing an embodiment using and arc-wiper (10) pivotally attached by an attachment pin (11), wherein the wiper moves through an arc (12).

Figure 8:
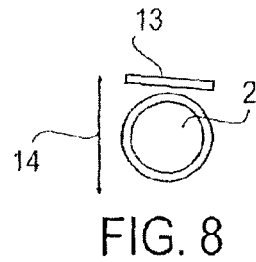

FIG. 8 is a schematic head-on view of the device showing an embodiment using a linear wiper (13) that moves through a path (14) perpendicular to the long edge of the wiper blade.

Figure 9:
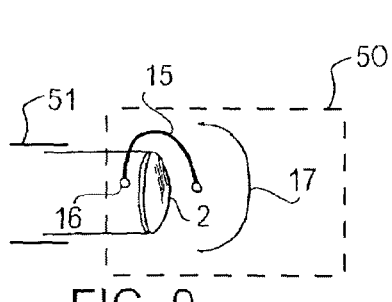

FIG. 9 is a schematic head-on view of the device showing an embodiment using a hemispherical sweep wiper (15) that moves through a hemispherical arc (17) similar to that of an eyelid. The hemispherical sweep wiper is pivotally attached by attachment pins (16) which act as fulcrums about which the wiper moves.

Figure 10:
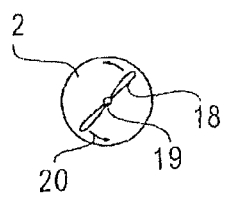

FIG. 10 is a schematic head-on view of the device showing an embodiment using a rotary wiper (18) that is pivotally attached by an attachment pin (19) mounted near the centre axis of the device and that moves in a rotational path (20) about the attachment pin in front of the lens.

Figure 11:
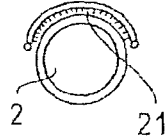

FIG. 11 is a schematic head-on view of the embodiment of FIG. 8 further including a brush element (21).

DETAILED DESCRIPTION OF EMBODIMENTS

Various embodiments are shown in FIGS. 1-11. In one preferred embodiment the invention is a device comprising a hollow device body (6) that is designed to fit over an endoscope. The body of the device may be rigid or flexible. The body of the device may be sufficiently flexible so as to conform and mold to the contour of the endoscope. Such flexibility may be achieved by using a soft, elastic material such as latex, rubber, plastic, or a woven fabric comprising latex or other elastic fibers. The hollow device body defines a lumen shaped and sized to receive an endoscope of a particular desired size. The distal end of the device body may be open or may be closed by means of a transparent window or lens cover (22). The device body (6) may define one or more internal guide channels (9), through some of which the lens cover film (3) is threaded. The lens cover film emerges out through a first guide slit (7), passes in front of the lens cover (22) and objective lens (2), and passes back into a second guide slit (8). Guide slits 7 and 8 are preferably parallel. The entire apparatus may also be designed to fit within a trocar.

Certain embodiments include a lens cover film that is wound onto a spool. For example, a flexible lens cover film (3) may be rolled onto a first spool (4) and systematically unrolled such that it passes in front of the objective lens (2) of the endoscope (1). The lens cover film (3) can be unrolled as needed to provide a clean and clear lens cover in front of the objective lens (2). The leading end of the lens cover film may be captured and wound onto on a second spool. By winding the lens cover film onto the second spool (5) the lens cover film is pulled from the first spool, along a pre-set travel path, passing in front of the objective lens, and wound onto the second spool. The spools may be positioned at any convenient location within or external to the device. The means of winding, unwinding, or moving the lens cover film may comprise many different design variations including spools, winches, geared mechanisms, manually operated and electrically operated elements. Although spools are described in various exemplary embodiments, the invention does not require that spools be used and the lens cover film may be retained by, released from, and captured by any suitable means. Designs of such means will be readily apparent to those of skill. For example the lens cover film may be retained in a folded configuration, folded up upon itself prior to release into a pre-set travel path.

The travel path may be defined by guides of various design sufficient to hold and guide the lens cover film along the pre-set travel path. The guide may include rails or slits through which the lens cover film passes. The guide is generally constructed as an integral part of the body of the device (6). The guide(s) and body of the device are further described in the detailed description.

In one embodiment, the flexible lens cover film (3) is retained on a first spool, unwound and captured on a second spool such that any particular section of the lens cover film passes in front of the objective lens only once. Having become soiled, the lens cover film is incrementally wound onto the second spool and a clean section of lens cover film moves into place in front of the objective lens. In an alternative embodiment, a section of the flexible lens cover film (3) may be moved alternately bi-directionally (i.e., back and forth) in front of the objective lens (or lens cover, if present). Movement of the lens cover film through the guide slits (7 and 8) will cause a section of the lens cover film to be cleaned, and this section will then be moved back in front of the objective lens. The cleaning action may be achieved by any type of wiper or washer system, for example using blade-type wipers or sponge wipers or brush wipers. In one embodiment the guide slits (7 and 8) may be edged with flexible wiper blades, made of, for example, silicone, rubber or plastic. As the lens cover film passes between the wiper blades, solid and liquid debris is removed, and the cleaned section of film may then be repositioned in front of the objective lens. This embodiment is advantageous because it requires the use of a shorter length of lens cover film and it requires less complex apparatus to retain the film.

The spools from and onto which the lens cover film is wound may be manipulated manually via dials mounted at the proximal end of the device. The dials may be positioned in any suitable disposition (for example see the control dials on a standard fiber-optic gastroscope). The spools may incorporate a spring biasing means (on the first spool) and a ratcheting means (on the second spool) such that the lens cover film is kept taut and can only be moved along the transit path in one direction. The control dials may incorporate gearing means by which the lens cover film may be drawn through the transit path at a slower or faster speed. The control of the movement of the spool or spools may be achieved via any means mechanically in some embodiments or electrically in other embodiments.

In certain embodiments the device is designed to have disposable elements or to be entirely disposable. Disposability is really a function of cost in relation to expense of sterilization. Heat and chemical sterilization is a relatively inexpensive process, but it may damage certain or the more delicate elements of an apparatus. For example, the lens cover film, depending on the material from which it is made, may be clouded or otherwise damaged by heat and oxidative agents (bleach). The lens cover film may be made from any transparent material such as polythene, acetate polyvinylchloride or other polymers which are inexpensive and may be disposable. The lens cover film may be made from any transparent material that has high melting temperature and can withstand the heat generated at the endoscope objective lens (2). In certain embodiments, the lens cover film may be augmented, coated, or treated with any additional component (of any means such as chemical or electrical) to achieve anti-fog capability. Surfactant, polymer, or corona treatment, for example, may provide a hydrophilic surface to the lens cover film that can provide anti-fog quality to the film. In other embodiments, the entire device may be disposable, dispensing with the need for sterilization altogether.

The body of the device is essentially a tube and may be made of any material (or any combination of materials) such as metal or molded plastic, for example polymers such as PTFE, polyvinylchloride, polypropylene, polyethylene, polyester or polyamide. Alternatively the body of the device may be in the form of a flexible sheath made at least partially from a material that will snuggly fit over and conform to the shape of the endoscope. Such materials include latex, rubber and woven elastic fabrics. The device may include a lens cover (22) at the distal tip, which may be made of any transparent material such as an acetate polymer and is able to withstand the heat generated at the objective lens (2) without melting or change.

The guide elements (7 and 8) accommodating the lens cover film may be of any dimension and design (linear, curvilinear, arc-like, or others) on cross sectional view of the device.

The surface of the lens cover film (3) may be made parallel to the surface of the objective lens (2) via any means, such as the use of support frames (23, 24), scaffolds, or specific device body distal tip design. The support frames, scaffolds, or distal device body tip may be made of any dimension, configuration, or material, such as nitinol, that may or may not have flexibility, inherent memory or elastic properties.

The present invention encompasses a number of different embodiments all of which remove debris and dirt from the viewing path of an endoscope. Some of these embodiments utilize a lens cover film that moves through a pre-set travel path, while others use various mechanical means to keep the viewing path and objective lens free of obstructive matter. Certain embodiments use wipers which may include flexible blades or brushes. The wipers may move through various different paths. In one embodiment, an arc-wiper (FIG. 7) is pivotally attached to the body of the device by an attachment pin and moves back-and-forth through an arc.

Alternatively, the wiper may move through a linear path (FIG. 8) whereby the blade moves back-and-forth perpendicular to the long edge of the wiper blade. The blade may be operated via strings or wires traversing through slits or holes or tunnels within the device body.

Another exemplary embodiment uses a wiper that moves through a hemispherical arc similar to that of an eyelid 50 (FIG. 9). The wiper is pivotally attached to the device body by attachment pins which act as fulcrums or hinges about which the wiper moves.

Another example of a wiper embodiment employs a rotary wiper (FIG. 10) that is pivotally attached by an attachment pin and mounted near the centre axis of the device. The wiper moves in a rotational path about the attachment pin removing dirt from front of the lens or lens cover.

Any of the wiper and brush embodiments may additionally employ a brush element or may use flexible blades of silicon, rubber, plastic or any other suitable substance. Multiple wipers and blades may optionally used in any embodiment.

The wipers may be impelled by any standard mechanical means such as an electric motor with power being transmitted via a standard cam mechanism. A standard reciprocal gear mechanism may be employed to produce a back-and-forth motion.

An alternate variation of the device of the invention employs a transparent lens cover coated with a coating that inherently repels fluids and other contaminants. Such a coating could, for example comprise a highly hydrophobic material such as polysiloxanes, fluoride compounds and a silane compounds. Such coatings are commercially available. Coatings can also be made so that they hold very little electrostatic charge and so that they form a very smooth molecular surface. All these qualities make a coated surface repellant to fluid and dirt. Such a coated lens cover could be employed alone or on combination with the other various embodiments of the invention.

The device of the invention may additionally incorporate various functional elements such as light sources, vacuum means, gas and liquid conduits, instrument conduits, biopsy instruments and various instruments used to help visualize a target or perform surgical procedures. For example, one or more light sources may be set into the distal end of the body of the device to provide illumination of a target. Such light sources may be provided by one or more electric lamps (incandescent or LED) mounted at the distal end of the device or the light may be transmitted via fiber optic conduits from a remote light source to the tip of the device. A remote light source may be provided separately from the device and may be coupled to the fiber optic cables by standard couplings. In another example, the body of the device may incorporate one or more vacuum conduits that may be used to produce suction at the distal tip of the device by which fluids such as blood and other body fluids may be removed. Such devices are well known in the art. Other alternate embodiments may employ conduits within the body of the device through which a gas can be pumped; for example, air or an inert or non-reactive gas is commonly pumped into the body cavity during procedures to enhance visualization, e.g. carbon dioxide, nitrogen, etc. Conduits may also transmit fluids such as sterile water and saline that may be used to wash and clean areas to be viewed. Such liquid may be removed via the suction tube. Other conduits may be used to deliver drugs such as local anesthetics and therapeutics. Additionally, a laser conduit may be employed to transmit laser light to a target, for example for ablation and cauterization of tissue. As mentioned above, other embodiments may include instruments such as biopsy needles and cutting instruments that may be operated remotely by the user from the proximal end of the endoscope.

The device of the invention may be fixed to the endoscope by any standard means. For example a lure-lock, strap, latch, pin or screw mechanism may be used to removeably clip the endoscope into the lumen of the invention and maintain the relative position of the endoscope and the device while in use.

The device of the invention may be used for endoscope of different objective lens orientation (such as 0 degree, 15 degree, 30 degree, 45 degree, 60 degree, and 70 degree endoscopes). Frames (flexible or rigid, of any material or design), scaffolds (flexible or rigid, of any material or design), or distal device tip design may be used to allow the surface of lens cover film (3) become parallel to the surface of objective lens (2), thereby allowing viewing without light deflection or image distortion.

The device of the invention may include transparent lens cover (22) integrated as part of the device body (6), thereby separating the device body lumen from device exterior surface. This would allow the use of endoscope (1) accommodated within the device body lumen without the need for sterilization of the endoscope, as the endoscope has no direct physical contact with body tissues. Additional slits or channels of various design or dimensions may be built within the device body to allow passage of air, fluids, debris, and/or endoscopic instruments. In fact, these additional slits or channels may be proximally associated with buttons, dials, openings, controls, or other designs and means and may be connected to vacuum source (for suction to remove debris from body cavity), air source (for pumping air into body cavity), or fluid irrigation source (for irrigation into body cavity). These features are particularly useful if the endoscope involved is a colonoscope, gastroscope, bronchoscope, and laryngoscope.

Although the examples in this disclosure concentrate upon embodiments where the device is separate from an endoscope and wherein the endoscope is placed within the lumen of the device, this invention additionally encompasses embodiments where the device to keep the objective lens free of debris is incorporated into the structure of an endoscope. In its most basic embodiment the integrated endoscope embodiment comprises an endoscope having lens cover film and a means for guiding the lens cover film in front of the objective lens. In another of the simplest embodiments, the endoscope is provided with an integrated wiper means that clears debris from the viewing path. Such embodiments may employ any or all the features of the separate embodiments.

In use, an endoscope, for example a laparoscope, is placed within the lumen of the body of the device of the invention. The objective lens of the laparoscope abuts or is in close proximity to the distal end of the tube. The distal end of the tube may be open or may terminate with a transparent window or lens cover. The entire device may be inserted into and through a standard laparoscopic trocar or a specially designed trocar. Via the trocar, the laparoscope can be placed inside the body cavity. During use the lens cover film may be moved in a preset travel path in front of the endoscope objective lens (and the lens cover, if present). The lens cover film may travel unidirectionally or bidirectionally. Any particular section may be used only once, or may be cleaned, for example by fixed wiper blades present at the guide slits, and reused by reversing the travel path of the lens cover film. In embodiments using wipers, the wiper may be activated to wipe the objective lens (and the lens cover, if present), so removing obstructive fluid and dirt.

The shape and size of the current invention may be selected for fitness for any specific purpose. For example, the present device may be used for any of the existing laparoscopes available in the market (such as 10 mm, 5 mm, 2 mm scopes) and may be used in conjunction with any of the existing laparoscopic trocars. Alternatively the invention may be used with specially designed laparoscopic trocars specifically designed to work with the present invention. For example, the body of the device may have a diameter of from 3 mm to 25 mm, or for example about 3 mm, 7 mm, 12 mm, 25 mm, 18 mm or 22 mm. The length of the device may be any length compatible with its function of maintaining a clear optical/visual pathway, and the device may (or may not) be shorter than the endoscope that is inserted into it. For example, the device may be from 4 cm to 30 cm in length, or for example about 5 cm, 7 cm, 10 cm, 14 cm or 18 cm in length. The body of the invention may be of variable fixed lengths, or it may be of dynamically adjustable length by using a telescoping design 51. The body of the invention is generally an elongated cylinder, though it may be of any suitable cross-sectional shape such as oval, triangular, square, polygonal, or polymorphous. The body of the invention may be rigid or may be flexible. A flexible body is desirable when using a flexible endoscope. The body of the device may be made from any biocompatible material, such as polyvinylchloride (PVC), polystyrene, polytetrafluoroethylene (PTFE), polypropylene, polyethylene, polyester or polyamide or other plastics or acrylics or rubber, or may be made of a metal such as a nickel-titanium alloy of stainless steel etc. The body of the device may be made from various manufacturing process(es) including heat shrinkage process. The lens cover film may be made from any transparent material such as polythene, polypropylene, polyacetates, polyvinylchloride or any other polymer materials. The lens cover film support scaffolds or frames (23 and 24) may be made from any material such as nitinol that may have memory or instrinsic elastic properties.

The present invention provides various advantages over the prior art devices and methods. The present invention provides devices that maintain a clear and unobstructed view through the objective lens of an endoscope while in use; devices that clear obstructive fluids and debris from the optical path of an endoscope while in use, devices that eliminate the need for the endoscope to be withdrawn from the patient on order that the objective lens may be cleaned, and devices that eliminate the need for endoscope sterilization during its use. This advantage of eliminating the need for endoscope withdrawal and objective lens cleaning is particularly important as removal and reinsertion of an endoscope slows surgical procedures, increases trauma, and can significantly impact surgical outcomes. Additionally, the present invention is simple and inexpensive to manufacture, simple to use and robust in use, and can be used with a variety of endoscopic devices.

Although the various exemplary embodiments of the present invention are directed to medical endoscopic uses, the present invention is not limited to such uses, and the device described may be used for any application in which it is important to maintain a clear optical path through the lens of a viewing instrument. The device can work equally with any type of viewing instrument or illuminating instrument to maintain a clear and unobstructed optical path. Such instruments may be used to visualize a target or to illuminate a target or both. The invention serves just as well to maintain a clear path for a beam of outgoing light as for a viewing lens. Alternative embodiments and applications include applications for sewer and drain cameras, which come in all manner of different formats. Some are similar to hand-held fiber-optic gastroscopes and can be inserted down a drain and through pipes. Others are large robotic instruments mounted on remote controlled power-trains that can be sent far along sewer pipes. Similar instruments are used to inspect gas and oil pipelines. In all these applications fouling of the optical pathway is a common and serious problem. Other applications of the current device may include providing unobstructed view to (1) lenses or cameras mounted on military vehicles or other motor vehicles such as race cars and (2) lenses or cameras used for wildlife filming or viewing. In such applications, the fouling of lenses and optical pathways by dust, fluids such as rain and mud are well known problems. Yet other embodiments include the use of the present invention to maintain a clear optical path for a photovoltaic device. The efficiency of such instruments, for example the conversion of solar energy into electrical energy by a solar panel, can be significantly diminished if small or microparticulate dust accumulates on the surface of the solar cells. This is particularly a problem encountered with the solar panels on the Mars rovers Opportunity and Spirit. Maintaining elevated levels of electrical output to the rover's storage batteries from such panels can significantly extend the useful life of the rover in such an extra-terrestrial mission. The device of the invention solves such problems in the same way as described above for the endoscopy examples. In the case of a viewing apparatus, the embodiment may involve the tubular system using a lens cover film that provides a continuously clear transparent covering for the lens or a camera and/or lamp. The lens cover film may be operated manually, electrically, robotically, or via other means. In other embodiments brushes and coated lenses may be used as described above.

It will be readily appreciated that various adaptations and modifications of the described embodiments can be configured without departing from the scope and spirit of the invention and the above description is intended to be illustrative, and not restrictive, and it is understood that the applicant claims the full scope of any claims and all equivalents.

The invention claimed is:

1. A device for maintaining a clear optical path comprising:
   a. an elongated hollow body comprising a proximal end and a distal end, wherein the elongated hollow body defines a lumen adapted to receive a viewing apparatus;
   b. a guide element coupled with the elongated hollow body, the guide element including a distal tip member attached distally to the distal end of the elongated hollow body such that the distal tip member projects beyond the distal end and lumen of the elongated hollow body;
   c. a transparent lens cover film, movably associated with the guide element, wherein the transparent lens cover film is guided by the guide element so as to describe a preset travel path passing in front of and substantially parallel to a lens of the viewing apparatus; and
   d. a section of the transparent lens cover film entirely covering the lens configured to move outside a line of sight of the lens when the first section is replaced by a second section of the transparent lens cover film.

2. The device of claim 1 wherein the lumen of the device is adapted to receive an endoscope or laparoscope.

3. The device of claim 2, wherein the distal end of the device is configured to allow the surface of the transparent lens cover film to pass in front of the lens of the viewing apparatus, so that the surface of the film is substantially parallel to the endoscope or laparoscope lens surface.

4. The device of claim 1 wherein the elongated hollow body further comprises a transparent window sealing the distal end, wherein the transparent window provides a complete separation of the luminal space and the exterior surface of the device.

5. The device of claim 1, wherein the preset travel path is unidirectional.

6. The device of claim 1, wherein the preset travel path is bidirectional.

7. The device of claim 1, wherein the elongated hollow body has a length that is adjustable.

8. The device of claim 1 wherein the elongated hollow body comprises at least one passageway allowing the passage of air, fluids, debris, or an instrument.

9. The device of claim 1, wherein the elongated hollow body is adapted to receive an illuminating apparatus.

* * * * *